United States Patent
Peetres et al.

(10) Patent No.: US 6,894,069 B2
(45) Date of Patent: May 17, 2005

(54) METHOD FOR TREATING PERINATAL ASPHYXIA IN A HUMAN OR ANIMAL NEONATE

(75) Inventors: Cacha Marie Pétronelle Cathérine Dorotheé Peetres, Utrecht (NL); Floris Groenendaal, Houten (NL); Frank Van Bel, Amstelveen (NL)

(73) Assignee: Universitair Medisch Centrum, Utrecht (NL)

( * ) Notice: Subject to any disclaimer, the term of this patent is extended or adjusted under 35 U.S.C. 154(b) by 89 days.

(21) Appl. No.: 10/362,051

(22) PCT Filed: Mar. 30, 2001

(86) PCT No.: PCT/NL01/00266

§ 371 (c)(1),
(2), (4) Date: Jul. 10, 2003

(87) PCT Pub. No.: WO01/74351

PCT Pub. Date: Oct. 11, 2001

(65) Prior Publication Data

US 2004/0002530 A1 Jan. 1, 2004

(30) Foreign Application Priority Data

Mar. 31, 2000 (EP) .......................... 002011914

(51) Int. Cl.⁷ .......................... A61K 31/4168
(52) U.S. Cl. ...................................... 514/398
(58) Field of Search ......................... 514/398

(56) References Cited

U.S. PATENT DOCUMENTS 5,464,858 A 11/1995 Griffith et al. .............. 514/399
5,854,234 A 12/1998 Bergmanis et al. ......... 514/312

FOREIGN PATENT DOCUMENTS

WO   WO 94/12165   6/1994

OTHER PUBLICATIONS

K.J. Escott et al., "Cerebroprotective effect of the Nitric Oxide Synthase Inhibitors, 1–(2–trifluoromethylphenyl) imidazole and 7–nitro indazole, afeter transient focal cerebral ischernia in the rate", Journal of Cerebral Blood Flow and Metabollism, 1998, pp. 281–287, XP–001008675.

E. Dzoljic et al., "Anticonvulsant activity of new and potent inhibitors of nitric oxide synthase", Brain Re. Bull., 1997, pp. 191–195, XP–001008673.

J.P. bolanos et al., "Roles of Nitric Oxide in Brain Hypoxia–Ischemia", Biochimica et Biophysica ACTA, 1999, pp. 415–436, XP–00937744.

K. Kumar, "Hypoxic–Ischemic Brain Damage in Perinatal Age Group", Indian Journal of Pediatrics, 1999, pp. 475–482, XP–000937788.

*Primary Examiner*—Phyllis G. Spivack
(74) *Attorney, Agent, or Firm*—Young & Thompson

(57) ABSTRACT

A selective inhibitor of neuronal nitric oxide synthase (nNOS) and of inducible nitric oxide synthase (iNOS), which does not substantially inhibit endothelial nitric oxide synthase (eNOS), can be effectively used for the treatment, in human or other mammalian neonates, of the effects of complications during childbirth. Such effects include perinatal asphyxia and hypoxia-ischemia. A very useful example of such a selective inhibitor is 2-iminobiotin.

3 Claims, 3 Drawing Sheets

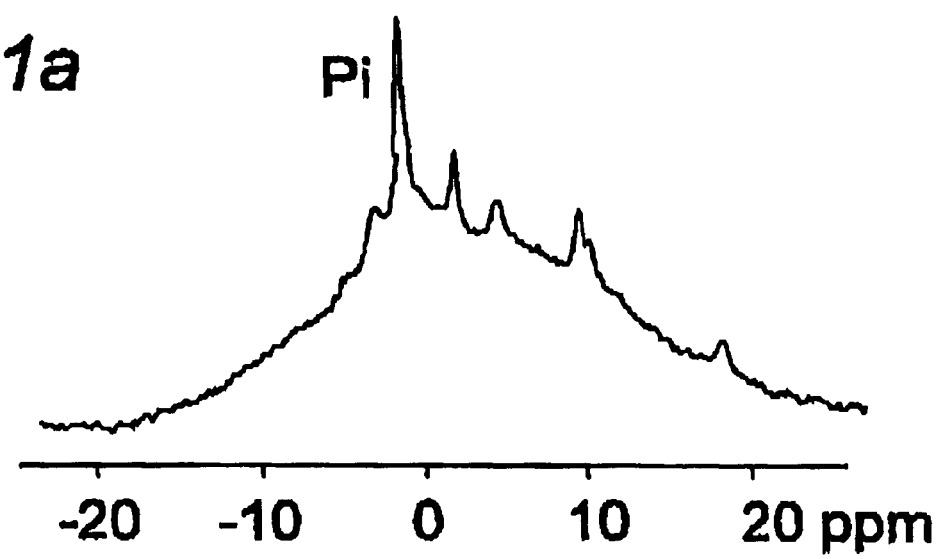
PLAC at 24 h post HI
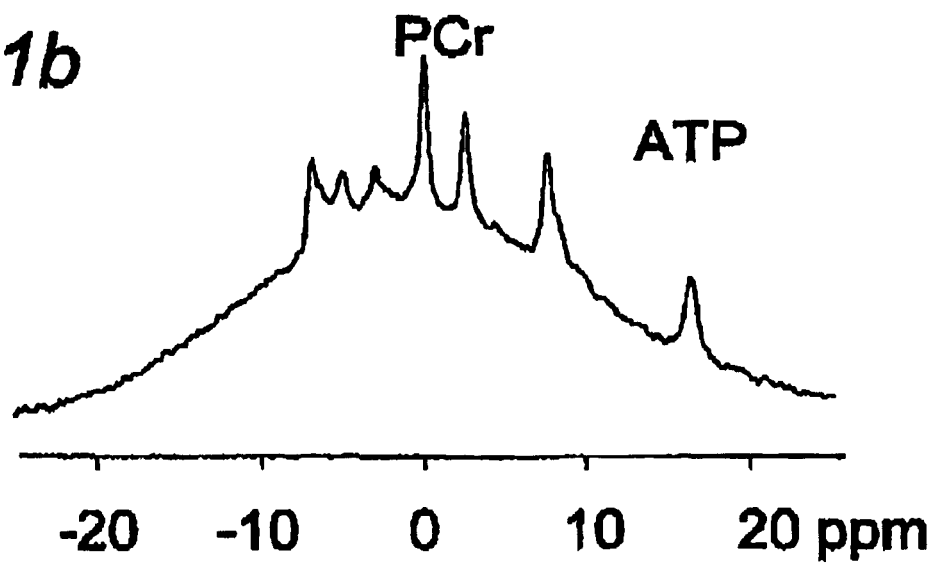
2-IB at 24 h post HI

METHOD FOR TREATING PERINATAL ASPHYXIA IN A HUMAN OR ANIMAL NEONATE

The present invention relates to pharmaceutical compositions that can be used to prevent and/or treat, in newborn babies the effects of complications that may occur during childbirth.

In particular, the invention relates to pharmaceutical preparations that can be used to prevent and/or treat, in newborn babies, the effects of perinatal asphyxia (=hypoxia-ischemia).

Specifically, the invention relates to pharmaceutical preparations that can be used to prevent and/or treat in newborn babies, brain damage or brain injury that may result from complications during childbirth such as perinatal asphyxia and/or hypoxia-ischemia.

It is envisaged that the preparations of the invention may also be used for veterinary purposes, e.g. to prevent and/or treat the effects of complications—such as those mentioned above—that may occur during the birth of any animal. For instance, it is known that up to 20% of young livestock before the age of weaning may die from asphyxiation. Thus, in another aspect, the invention may provide suitable veterinary preparations.

It is also envisaged that the invention may be used to prevent and/or treat, in people of all ages, the complications and (after-) effects that occur during result from for instance brain cell injury. Thus, in yet another aspect, the invention also provides suitable pharmaceutical compositions for the treatment of such complications and/or (after-) effects.

Perinatal asphyxia is a serious complication of childbirth which affects about 1% of newborns world-wide. It may lead to hypoxia-ischemia or more generally to injury to the baby due to lack of (sufficient) oxygen. The incidence of stroke in the western world is 127 per 100,000.

In particular at risk of such damage is the brain. For instance, hypoxia-ischemia during childbirth may result in neonatal encephalopathy, cerebral palsy, mental retardation, learning disabilities, epilepsy or other long-term effects. For a large part, these effects are caused by excessive formation of free radicals such as superoxide and hydroxyl radicals. These radicals are especially formed directly after a period of hypoxia-ischemia when reoxygenation and reperfusion are re-established. Together with NO (nitric oxide) superoxide reacts to peroxynitrite, which attacks the brain cell membranes, resulting in lipid peroxidation and eventually cell death.

It has been suggested in the art to prevent or treat the above effects by administering to neonates that are at risk, free radical scavengers and/or xanthine oxidase inhibitors such as allopurinol ("ALLO") or non-protein bound iron chelators such as deferoxamine ("DFO"). In a pilot study in newborn babies and in experimental studies it has been shown that allopurinol and deferoxamine reduce fee radical-induced brain damage in newborns to some extend, these compounds, however, are still not fully satisfactory.

Since excessive biosynthesis of NO results in perinatal destruction of neurons, the use of nitric oxide synthase inhibitors seems to be promising in reducing brain injury after perinatal hypoxia-ischemia. However, data concerning non-specific NOS inhibitors after hypoxia-ischemia are conflicting: for instance it has been shown that $N^G$-nitro-L-arginine (NNLA) compromised cerebral energy status during and after hypoxia-ischemia (HI) in newborn piglets (Groenendaal et al, *Pediatric Res.* 45 (1999) 827–833), whereas L-nitro-arginine methyl ester (L-NAME) was neuroprotective in neonatal rats (Palmer et al., *Pediatric Res.* 41 (1997) 294A). Nowadays, three types of NOS isoforms have been characterised: neuronal, inducible and endothelial NOS. Using selective NOS inhibitors and transgenic animals it has been suggested that the NOS isoform determines whether it acts neuroprotective or neurotoxic upon HI (Bolanos and Almeida, *Biochim. Biophys. Acta* 1411 (1999), 415–436). Johnston et al (*Semin. Neonatal.* 2000(5): 75–86) showed that 7-nitroindazole, mainly a neuronal NOS inhibitor but only injectable intra-peritoneally, was effective in reducing apoptosis and reducing the levels of citrulline. Higuchi et al (*Eur. J. Pharmacology* 342 (1998) 47–49) and Tsuji et al (*Pediatric Res.* 47 (2000), 79–83) reported that aminoguanidine, mainly an inducible NOS inhibitor, reduced infarct volumes in neonatal rats. On the other hand, endothelial NOS knock-out mice were highly sensitive to cerebral ischemia, suggesting a role for eNOS in cerebral perfusion. NOS inhibitors with potential usefulness in reducing brain injury after perinatal HI need to be water soluble for rapid intravenous injection in mother or newborn child/animal and need to be transported to the brain and be selective inhibitive for neuronal and inducible NOS.

Until now no accepted therapy is available for asphyxiated infants. Therefore, there is a need for pharmaceutical preparations that may be used to prevent and/or treat, in newborn babies, the effects of complication that may occur during childbirth.

In addition, as already mentioned above, there is also a need for veterinary preparations that can be used for the same or similar purposes is newborn animals. Also, there is a need for pharmaceutical preparations that can be used to prevent and/or treat (the effects of) brain cell injury in people of all ages.

According to the present invention, it has been found that 2-iminobiotin and other specific neuronal and inducible NOS inhibitors, can be used to prevent and/or treat the above-mentioned effects. In particular, in in vivo studies involving piglets (vide the Experimental Part below), it was found that 2-iminobiotin is more effective in preventing and/or treating these effects than either allopurinol and/or deferoxamine, e.g. about 60% more effective then placebo treatment and about 25% more effective than treatment with allopurinol and/or deferoxamine.

Therefore, the NOS inhibitors to be used according to the present invention should be capable of inhibiting neuronal NOS (nNOS=brain NOS), as well as inducible NOS (iNOS). However, the NOS inhibitor should not significantly inhibit endothelial NOS (eNOS). Specifically, the inhibiting effects on nNOS and on iNOS should correspond to an inhibitory concentration $IC_{50}$ of 150 $\mu$M or lower, preferably 50 $\mu$M or lower, whereas the inhibiting effect on eNOS, if any, should correspond to an inhibitory concentration $IC_{50}$ of 250 $\mu$M or higher, preferably 500 $\mu$M or higher. In particular the inhibitory concentration of either nNOS or iNOS or both should be at least a factor 5, preferably at least a factor 50 lower than the inhibitory concentration on eNOS.

The inhibitor is preferably highly soluble in aqueous medium. In general the solubility should be such that a prophylactically or therapeutically effective amount of the inhibitor is soluble in 100 ml or less, preferably in 50 ml or less aqueous medium for newborn babies. In particular the inhibitor has a solubility in aqueous medium of at least 50 $\mu$mol per 100 ml, preferably at least 150 $\mu$mol per 100 ml.

It was found that 2-iminobiotin and other nNOS, iNOS, non-eNOS inhibitors such as S-benzylisothiourea, L-thiocitruline, $N^G$-monoethyl-L-arginine, TRIM (1-(2-trifluro-methylphenyl)imidazole), meet the requirements of sufficient specificity and solubility.

Thus, in a first general aspect, the invention relates to a pharmaceutical composition, comprising a NOS inhibitor such as 2-iminobiotin or a pharmaceutically acceptable salt thereof, and optionally at least one pharmaceutically acceptable carrier, excipient or adjuvant.

In a first specific aspect, the invention relates to a pharmaceutical composition for the prevention and/or treatment in neonates of the effects of complications during childbirth, said preparation comprising a selective NOS inhibitor as defined above, and optionally at least one pharmaceutically acceptable carrier, excipient or adjuvant.

In particular, this aspect of the invention relates to such a pharmaceutical composition for the prevention and/or treatment in neonates of the effects and consequences of perinatal asphyxia (=hypoxia-ischemia); for the prevention and/or treatment in neonates of brain injury or brain damage following complications during birth, including but not limited to neonatal encephalopathy, cerebral palsy, mental retardation, learning disabilities and epilepsy; and/or for the prevention and/or treatment in neonates of a reduction in cerebral energy status and/or a reduction in electrical brain activity following complications during birth, lactate formation (metabolic acidosis), low apgar scoring scale during childbirth.

In a second specific aspect the invention relates to the use of the selective NOS inhibitor, such as 2-iminobiotin or a pharmaceutically acceptable salt thereof, in the preparation of a pharmaceutical composition for the prevention and/or treatment in neonates, of the effects of complications during childbirth as described above.

In another specific aspect, the invention relates to a pharmaceutical composition for the prevention and/or treatment of (the effects of) brain cell injury in people of all ages, said preparation comprising an inhibitor as described above, and optionally at least one pharmaceutically acceptable carrier, excipient or adjuvant, and to the use. Brain cell injury may be associated with focal ischemia, thrombotic stroke, global ischemia, neuro-degeneration, infections such as meningitis, and traumatic brain injury. Also, the invention relates to the use of 2-iminobiotin or related selective NOS inhibitor or a pharmaceutically acceptable salt thereof in the preparation of a pharmaceutical composition for the prevention an/or treatment of (the effects of) brain cell injury in people of all ages.

In another general aspect, the invention relates to a veterinary composition, said preparation comprising a selective inhibitor as described above and optionally at least one carrier, excipient or adjuvant acceptable for veterinary purposes.

In a further specific aspect, the invention relates to a veterinary composition for the prevention and/or treatment in newborn animals of the effects of complications during the birth of such an animal, said preparation comprising the inhibitor, and optionally at least one carrier, excipient or adjuvant acceptable for veterinary purposes and to their use in the preparation of a veterinary composition for the prevention and/or treatment in newborn animals of the effects of complications during the birth of such an animal.

The term "selective NOS inhibitor" in the context of the present invention means a compound capable of inhibiting inducible nitric oxide synthase (iNOS) as well as neuronal nitric oxide synthase (nNOS) but not or much less strongly inhibiting endothelial form of nitric oxide synthase (eNOS), as defined above.

The term "complications during childbirth" includes any irregularity or complication that may occur—and/or that may have occurred—during childbirth and that may cause harm to the newborn, including but not limited to those irregularities or complications that may occur prior to childbirth, while the baby is being born, or shortly thereafter; and irrespective of the cause(s) thereof (e.g. with the baby itself and/or with the mother).

In particular, the term "complications during childbirth" includes any such irregularities/complications that may lead to—or that may put the baby at risk of—asphyxiation (=hypoxia, ischemia or generally lack of sufficient supply of oxygen to the baby) and/or to any tissue or organ of the baby; and/or any such irregularities or complications that may lead to brain damage or injury in the baby or that put the baby at risk thereof. These may include complications such as mental retardation, neonatal encephalopathy, learning disabilities and epilepsy.

Thus, in particular, the pharmaceutical preparation of the invention may be used to prevent and/or treat in neonates, the effects of perinatal asphyxia (=hypoxia-ischemia); to prevent and/or treat, in neonates, brain injury or brain damage following complications during birth, including but not limited to neonatal encephalopathy, cerebral palsy, mental retardation, learning disabilities and epilepsy; and/or to prevent and/or treat, in neonates, a reduction in cerebral energy status and/or a reduction in electrical brain activity following complications during birth.

With respect to the above and the further disclosure herein, it will be clear to the skilled person that in or for those aspects wherein the invention relates to veterinary preparations and/or veterinary uses of (the compositions containing fir appropriate iNOS and nNOS inhibitor, the above applies analogously, e.g. by reading (newborn) animal instead of (newborn) baby/child and by reading mother of the (newborn) animal instead of mother of the (newborn) baby or child.

The pharmaceutical compositions of the invention are intended to be administered to newborn babies, and in particular to neonates that suffer from, are expected to suffer from, or are otherwise judged to be at risk from the above-mentioned effects. Also, the pharmaceutical composition can be administered to the mother of the fetus, when an asphyxiated newborn is expected. For the purposes of the present invention, the terms "newborn baby" and "neonate" include babies born by natural childbirth as well as babies that have been delivered by for instance caesarean section, and also include babies that have been born prematurely and/or the birth of which has been artificially induced. The term mother refers to the mother of the fetus or the newborn baby, including natural, inseminated, induced and carrier mothers.

Analogously, the veterinary preparations/compositions of the invention are intended to be administered to newborn animals, especially mammals, such as piglets, lambs, horses, goats etc.

Whether any newborn baby is at risk of any of the above effects—or more generally whether treatment with the compositions of the invention is indicated—will usually be determined by the clinician, taking into account any complications and/or irregularities that may have occurred shortly before or during childbirth. Babies at risk may be determined by decelerations in the fetal heart rate patterns or in the cardiotocogram (CTG), meconium-stained anmiotic fluid, metabolic acidosis in microblood samples and loss of fetal movement or other symptoms known to the skilled obstetrician. Also, at birth, babies subjected to perinatal asphyxia may be identified by ascertaining the presence of (biphasic) changes in brain activity or brain energy level, for instance using magnetic resonance techniques, including but not limited to those described in the Experimental Part below; but also an lactate values in blood, low Apgar scores, blood gas values, the clinical condition and the electroencephalogram EEG).

Usually, treatment of a neonate with the compositions of the invention will be carried out shortly after childbirth, e.g. during the "window" for therapeutic intervention. Usually, this window spans the first day following childbirth, and in particular the first 3–24 hours following childbirth. However, if an asphyxiated baby can be expected, treatment will be carried out in the mother before the expected labour, in particular about 24 h before labour.

As part of such treatment, the preparations of the invention will generally be administered to the neonates in one or more pharmaceutically effective amounts, and in particular in one or more amounts that are effective in preventing and/or treating the above-mentioned effects. Such treatment may involve only single administration of a composition of the invention, but usually—and preferably—involves multiple administrations over several hours or days, e.g. as part of or according to an administration regimen or treatment regimen. Such a treatment regimen may for instance be as follows: every 4 hours intravenously injection of the substance during the first 24 hours.

Usually, the amounts of NOS inhibitor administer to the neonate will correspond to between 0.01 and 250 mg per kg body weight preferably between 0.1 and 10 mg/kg. These amounts refer to the active component and do not include carrier or adjuvant materials such as carbohydrates, lipids or proteins or the like, that may originate from the production of the active inhibitors or may be used in assisting administration or targeting. These amounts may be administered as a single dose or as multiple doses per day, or essentially continuously over a certain period of time, e.g. by continuous infusion.

Treatment may be continued up to 24 hours after asphyxia, or otherwise until the neonate is judged no longer to be at risk of the effects mentioned above.

However, the treatment, especially the preventive treatment may also involve administration of the appropriate NOS inhibitor to the mother before or during partition, preferably by intravenous injection. The amounts to be administered can then be the same or higher, depending on the placental transfer and the metabolism, the first pass effect in the liver and the distribution volume of the compound. Thus the amounts administered to the mother may vary between e.g. 0.01–250 mg of active component per kg of the body weight of the mother.

The preparations of the invention may contain 2-iminobiotin or other suitable inhibitors as the free compound or as a pharmaceutically acceptable salt; optionally in combination with one or more pharmaceutically acceptable carrier, adjuvants and/or excipients.

The pharmaceutical preparation of the invention may be administered in any suitable manner—e.g. as known per se for allopurinol and/or deferoxamine—including but not limited to oral administration, intravenous administration, subcutaneous administration and/or intramuscular administration. Thus, the pharmaceutical preparation of the invention may be in any form suitable for such administration, including but not limited to tablets, capsule, powders, sachets, solutions, suspensions, emulsions, elixirs, droplet, sprays, etc. These may be formulated in a manner known per se, optionally using one or more suitable pharmaceutically acceptable adjuvants, excipients or carriers; and may also be suitably packaged, e.g. in a suitable container such as a vial or a bottle.

Preferably, the pharmaceutical preparations of the invention are administered intravenously, such as by injection and in particular by (drip-) infusion. Preparations suitable for such intravenous administration may for instance be prepared by mixing 2-iminobiotin or a salt thereof with water or a pharmaceutically acceptable buffer or solution such as normal saline. For this purpose, the pharmaceutical preparations of the invention may also be (marketed) in a form that can be—and/or at is intended to be—dissolved or reconstituted to provide a preparation suitable for intravenous administration. For instance, the preparations of the invention may be in the form of a powder (e.g. in a vial or sachet) that is dissolved or otherwise reconstituted with water or a physiologically acceptable solution or buffer just prior to injection or infusion.

The pharmaceutical compositions of the invention will contain the inhibitor in a suitable amount, preferably as a unit dose; e.g. in amounts that allow for convenient administration of the doses indicated above.

Besides the 2-iminobiotin or other specific NOS inhibitor, the preparations of the invention may also contain one or more other therapeutically effective substances, and in particular one or more active substances that are suitable and/or intended for administration to neonates, e.g. for treating and/or preventing the above and/or other effects of complications during childbirth. The preparations of the invention may also contain one or more further pharmaceutically acceptable components or ingredients, for instance one or more of the usual ingredients or components for use in infusions for neonates.

Although the invention is not limited to any specific explanation or mechanism, it is assumed that 2-iminobiotin acts by inhibiting neuronal and inducible Nitric Oxide Synthase (NOS I+II), which in turn reduces the (neuronal) formation of nitric oxide and thereby the formation of peroxynitrite which may attack the brain cells or their membranes. In doing so, 2-iminobiotin surprisingly does not show the adverse effect of (also) inhibiting the endothelial form of nitric oxide synthase (eNOS); or at least is more specific in inhibiting nNOS and iNOS relative to eNOS, thereby leaving the cerebral perfusion intact.

Furthermore, although the invention has been described above with reference to 2-iminobiotin (the preferred compound of the invention), it is envisaged that any other available specific neuronal nitric oxide synthase inhibitor e.g. might give comparable results. Some non-limiting examples of such suitable selective nitric oxide synthase inhibitors may include S-benzyl-isothiourea (such as the hydrochloride thereof), α-guanidinoglutaric acid (GGA); L-thiocitrulline, L-$N^5$-(1-iminoethyl)ornithine (L-NIO) (such as the hydrochloride thereof); $N^G$-monomethyl-L-arginine (NMEA); TRIM or pharmaceutically and/or veterinary acceptable salts thereof.

The invention will now be illustrated by means of the following Figures and examples, which do not limit the scope of the invention. In the Figures:

FIGS. 1A and 1B show 31P-MR spectra of a representative PLAC treated piglet (FIG. 1A) and a representative 2-IB treated piglet (FIG. 2B) at 24 h post HI.

EXPERIMENTAL PART

Materials and Methods

Following anaesthesia and instrumentation 37 newborn Dutch store piglets (1–3 days old) were subjected to HI by occluding both common carotid arteries with inflatable cuffs and reducing the fraction of inspired oxygen for 60 min. MRS was performed continuously before, during and up to 3 h after start of HI and repeated 24 h post HI. During hypoxia FiO2 was reduced >on-line=until PCr/Pi had decreased to at least 25% of baseline values. Immediately after HI the piglets received either placebo (PLAC; n=10), ALLO (20 mg/kg iv; n=10), DFO (10 mg/kg iv; n=10) or 2-IB (150 μM i.v.; n=7). Before HI and from 3 to 24 h post HI the piglets were monitored using aEEG for electrical brain activity determination. A neurologic scoring system was used ranging from 4 (normal) to 0 (flat trace). For 1H-MRS a PRESS sequence with CHESS water suppression was used to define a 1.7 ml periventricular voxel (TR 6 s, TE 144 ms, and nt=32 or 64). 31P-MRS was done using a 4 cm-diameter surface coil for excitation and detection (TR 10 s, nt=32). Peak amplitudes of PCr, Pi, Lac and NAA were determined with time domain fitting procedures (VARPRO). Paired t-tests were used to compare measurements at 24 h versus baseline; repeated ANOVA served to monitor for trends between treatment groups.

Results

Figure 2A:
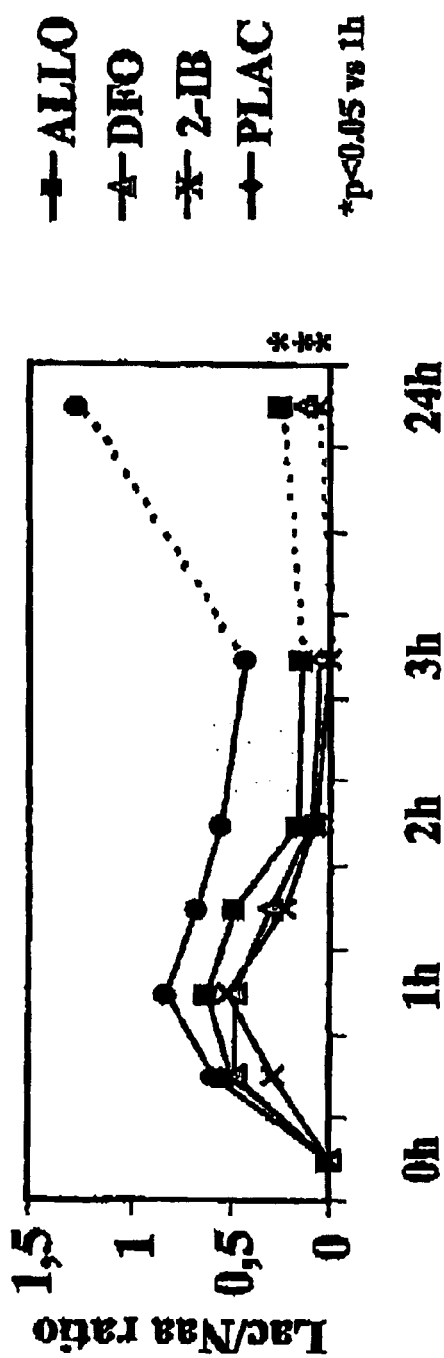
FIGS. 2A and 2B are graphs showing PCr/Pi % (FIG. 2A) and Lac/NAA ratios (FIG. 2B) from normoxia until 24 h post HI in PLAC, ALLO, DFO and 2-IB-treated piglets.
Figure 2B:
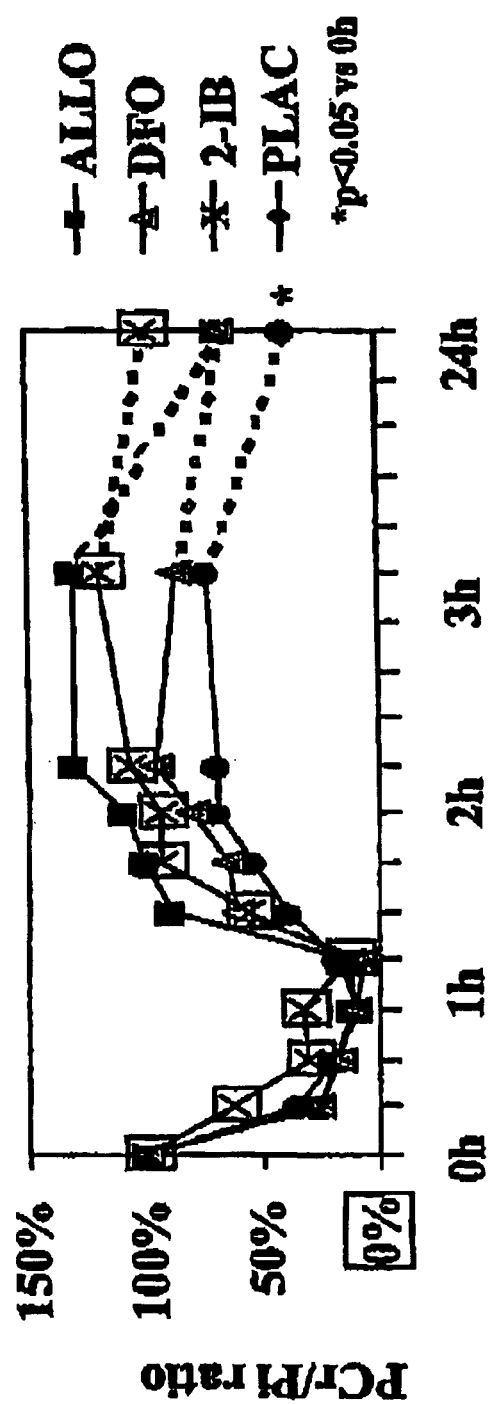
Figure 3:
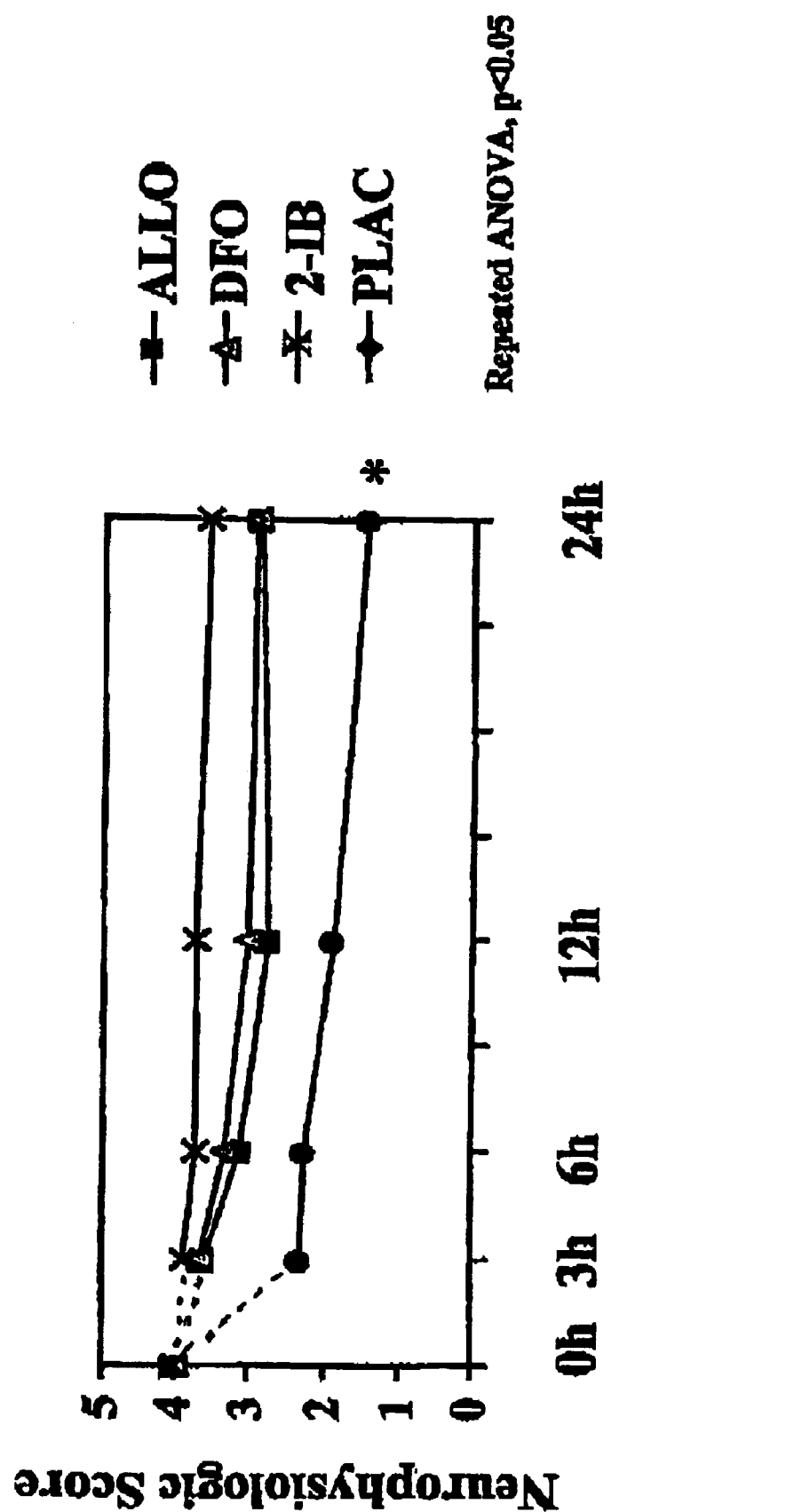
FIG. 3 shows an EEG for PLAC, ALLO, DFO and 2-IB treated piglets before HI, and at 3, 6, 12 and 24 h post HI.

Three piglets in the PLAC group and 1 piglet in the ALLO group died due to HI complications at respectively 5, 9 and 19 h and 18 h post HI, 1 piglet died at 13 h in the DFO group because of hypovolemic shock and 1 in the 2-IB group due to sepsis. 31P-MR spectra of a representative PLAC and 2-IB-treated piglet are shown in FIG. 1 at 24 h post HI. Secondary energy failure, defined as a secondary fall in PCr/Pi is observed in the PLAC, but not in the 2-IB piglet. PCr/Pi as percentage of baseline and Lac/NAA ratios from normoxia to 24 h post HI for all treatment groups presented in FIG. 2. For the 2-IB group 24 h post HI values were identical to baseline values of PCr/Pi and Lac/NAA. For PLAC-treated piglets PCr/Pi was significantly decreased and Lac/NAA significantly increased at 24 h post HI. FIG. 3 shows the neurologic score for all treatment groups. Using repeated ANOVA a significant difference was demonstrated between PLAC and 2-IB, ALLO and PFO (all p<0.05).

Histological analysis at 24 h post the hypoxia-ischemic period revealed more alive cells in the 2-IB treated piglets in the brain regions at risk after HI (hippocampus, cortex, striatum and cerebellum), less necrosis and a better preserved structural architecture. Furthermore, immunohistochemistry for nitrotyrosylation in the affected areas (a product being formed by the interaction of peroxynitrite on tyrosine residues) showed no staining in the 2-IB treated piglets, whereas the placebo treated piglets had a considerably level of nitrotyrosylation. This suggests that 2-IB can pass the blood brain barrier after hypoxia-ischemia and that it actually reduces the amount of peroxynitrite that is being formed in brain cells.

Conclusion

Whereas ALLO en DFO prevented partly the reduction in PCr/Pi ratios at 24 h post HI, 2-IB preserved completely cerebral energy stats at 24 h post HI. 2-IB and to a lesser degree ALLO and DFO prevented increment of Lac/NAA at 24 h post HI and preserved electrical brain activity. Histology confirmed this outcome including less nitrotyrosylation staining in the 2-IB treated animals. We speculate that the remarkable preservation of the cerebral energy status by 2-IB is due to prevention of the formation of peroxynitrite following hypoxia-ischemia in the newborn piglet.

What is claimed is:

1. A method for treating perinatal asphyxia in a human or animal neonate having neonatal asphyxia or being at risk of developing said asphyxia, comprising administering to said neonate an effective amount of a pharmaceutical composition comprising 2-iminobiotin, as a neuronal nitric oxide synthase inhibitor and an inducible nitric oxide synthase inhibitor but not an endothelial nitric oxide synthase inhibitor, to treat the effect of perinatal asphyxia.

2. The method according to claim 1, wherein the composition is suitable for intravenous administration.

3. The method according to claim 2, wherein said administered to said neonate after birth.

* * * * *